(12) United States Patent
Han et al.

(10) Patent No.: US 6,337,404 B1
(45) Date of Patent: Jan. 8, 2002

(54) DIAMINE HOLE TRANSPORT AGENT AND ORGANIC ELECTROLUMINESCENT DEVICE CONTAINING SAME

(75) Inventors: Ki-jong Han, Daejeon; Youngkyoo Kim, Pusan; Jae-Gyoung Lee, Kyungki-do; Dong-Kwon Choi, Seoul, all of (KR)

(73) Assignee: Nessdisplay Co., Ltd., Suwon-si (KR)

( * ) Notice: Subject to any disclaimer, the term of this patent is extended or adjusted under 35 U.S.C. 154(b) by 0 days.

(21) Appl. No.: 09/461,238

(22) Filed: Dec. 16, 1999

(30) Foreign Application Priority Data

Dec. 17, 1998 (KR) .............................. 98-55797
Jul. 1, 1999 (KR) ............................. 99-26278

(51) Int. Cl.$^7$ .......................... C07D 209/82; H01J 1/62
(52) U.S. Cl. ...................... 548/440; 428/690; 428/917; 313/502; 313/503; 313/504
(58) Field of Search ................................ 564/307, 308; 548/440; 428/690, 917; 313/502, 503, 504

(56) References Cited

PUBLICATIONS

Chem Abstract Online Printout 128:68313; Abstract of JP 09298089 Published 11/18/19997; See RN 15556–65–6.*

* cited by examiner

Primary Examiner—Samuel Barts
(74) Attorney, Agent, or Firm—Jacobson Holman, PLLC

(57) ABSTRACT

A novel diamine compound of formula (I) of the present invention having a high glass transition temperature is useful as an improved hole transport agent, and an organic electroluminescent device containing the diamine compound of formula (I) has good thermal and mechanical stabilities, and prolonged lifetime.

2 Claims, 9 Drawing Sheets

DIAMINE HOLE TRANSPORT AGENT AND ORGANIC ELECTROLUMINESCENT DEVICE CONTAINING SAME

FIELD OF THE INVENTION

The present invention relates to a novel diamine hole transport agent, and, more particularly, to a novel diamine compound having an improved hole transport capability and a high glass transition temperature, and an organic electroluminescent device containing same.

BACKGROUND OF THE INVENTION

Generally, an organic electroluminescent device has a laminated structure comprising a transparent electrode layer, a metallic electrode layer, and an organic interlayer including an organic luminescent layer arranged between the two electrodes. The organic interlayer comprising an organic luminescent layer may further include a hole transport layer sandwiched between the transparent electrode layer and the organic luminescent layer, and may still further include an electron transport layer inserted between the metallic electrode layer and the organic luminescent layer, often in a multilayer configuration to increase luminous efficiency.

Hitherto, aromatic tertiary amines such as tetraphenylbiphenyldiamine(TPD), N-phenylcarbazole, 4,4'-bis[N-(1-naphthyl)-N-phenylamino]biphenyl(NPB) have been used in forming a hole transport layer.

However, due to the fact that the above-mentioned compounds have low glass transition temperatures ranging from 60 to 95° C., electroluminescent devices containing such hole transport agents have low heat stability, bad resistance to external impact, and short lifetime under hard environment.

Therefore, there has existed a need to develop a novel compound having a high glass transition temperature for use in an electroluminescent device with improved hole transport capability.

SUMMARY OF THE INVENTION

Accordingly, it is a primary object of the present invention to provide a novel compound having an improved hole transport capability and a high glass transition temperature, and an organic electroluminescent device containing same.

In accordance with one aspect of the present invention, there is provided a diamine compound of formula (I):

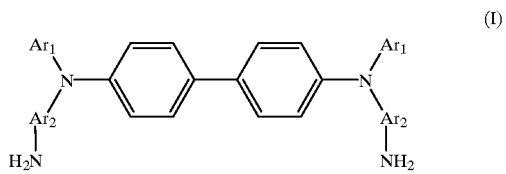

(I)

wherein, $Ar_1$ is a phenyl or biphenyl group, and $Ar_2$, is a phenylene or

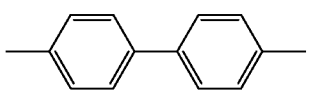

group, $Ar_1$ and $Ar_2$ being optionally fused to form, together with the nitrogen atom attached thereto, substituted carbazole derivative.

BRIEF DESCRIPTION OF THE DRAWINGS

The above and other objects and features of the present invention will become apparent from the following description thereof, when taken in conjunction with the accompanying drawings wherein.

Figure 1:
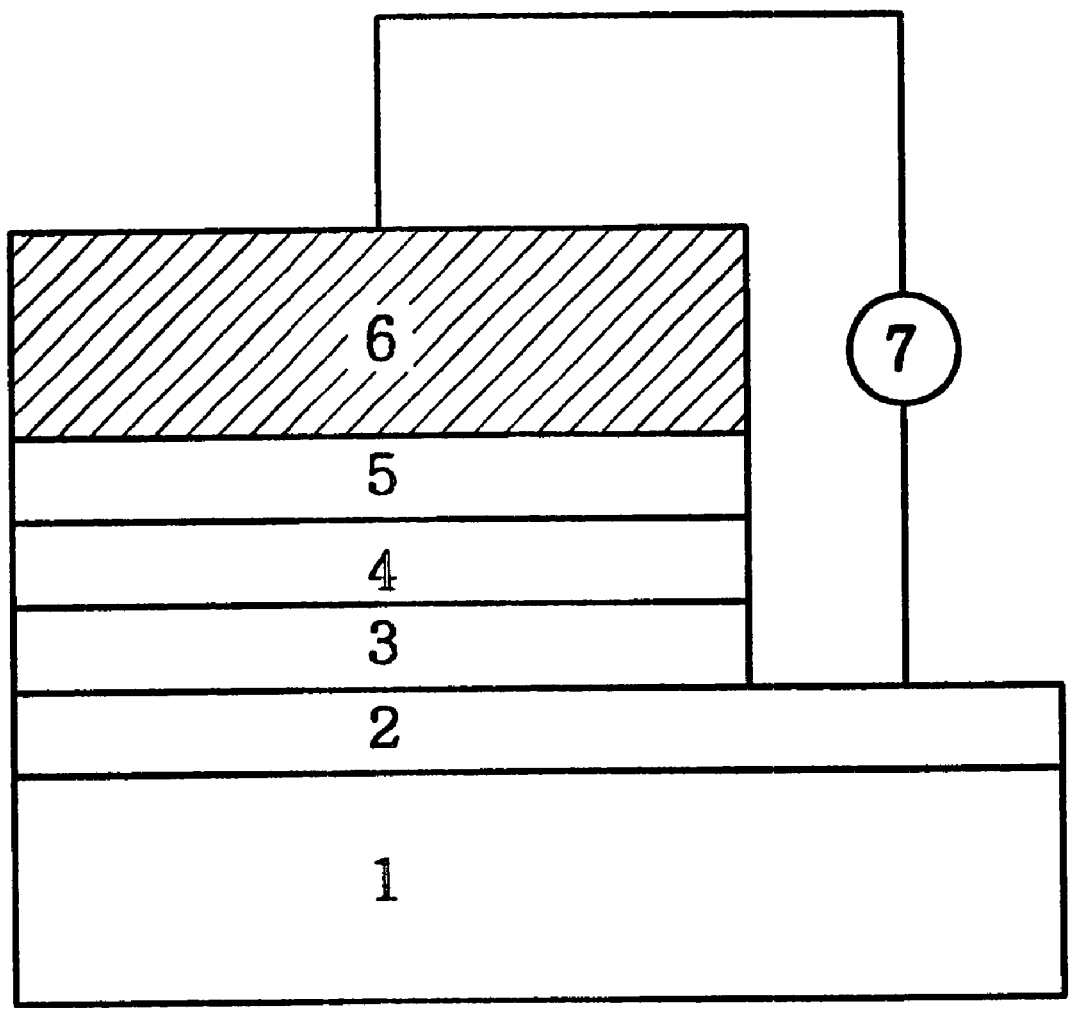
FIG. 1 is a schematic diagram of an organic electroluminescent device prepared in accordance with one embodiment of the present invention.

DETAILED DESCRIPTION OF THE INVENTION a diamine derivative of formula (I) of the present invention contains two groups of primary amine as well as two groups of tertiary amine, and representative examples thereof have the structures of formulae (Ia) to (Ic):

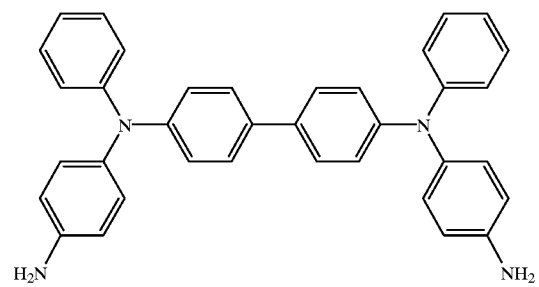

(Ia)

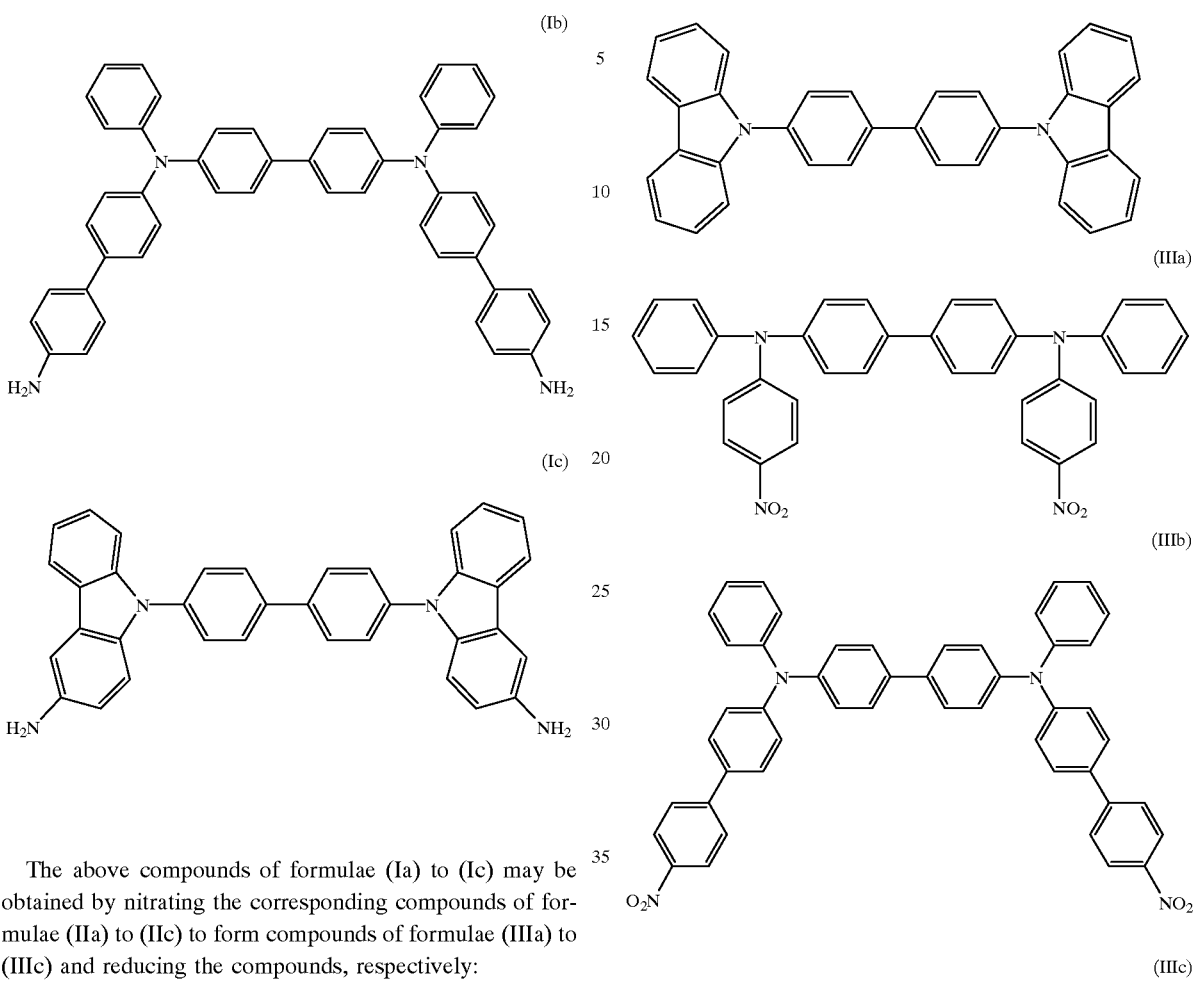

The above compounds of formulae (Ia) to (Ic) may be obtained by nitrating the corresponding compounds of formulae (IIa) to (IIc) to form compounds of formulae (IIIa) to (IIIc) and reducing the compounds, respectively:

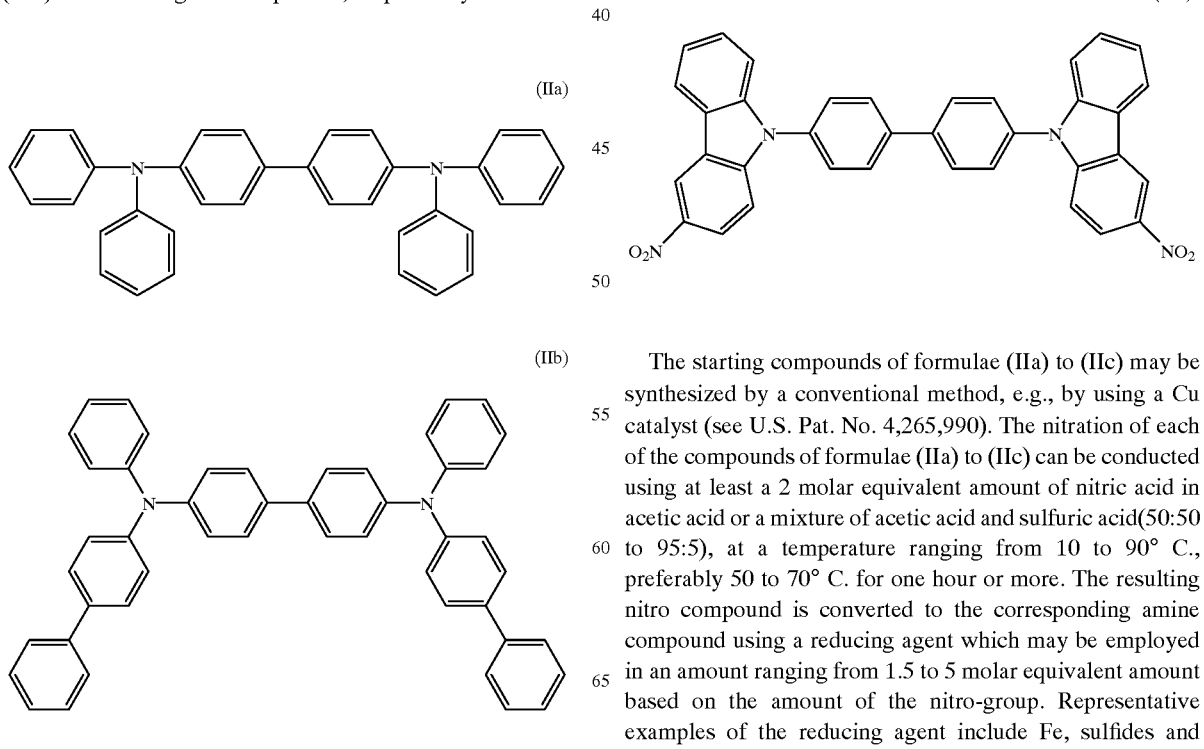

The starting compounds of formulae (IIa) to (IIc) may be synthesized by a conventional method, e.g., by using a Cu catalyst (see U.S. Pat. No. 4,265,990). The nitration of each of the compounds of formulae (IIa) to (IIc) can be conducted using at least a 2 molar equivalent amount of nitric acid in acetic acid or a mixture of acetic acid and sulfuric acid(50:50 to 95:5), at a temperature ranging from 10 to 90° C., preferably 50 to 70° C. for one hour or more. The resulting nitro compound is converted to the corresponding amine compound using a reducing agent which may be employed in an amount ranging from 1.5 to 5 molar equivalent amount based on the amount of the nitro-group. Representative examples of the reducing agent include Fe, sulfides and hydrogen, among which NaSH is preferred. The reduction can be carried out in an alcohol solvent such as ethanol, propanol and butanol, or in a mixture of alcohol and water(50:50 to 95:5), at a temperature ranging from 60 to 150° C., preferably 80 to 120° C.

Alternatively, the compounds of formulae (Ia) and (Ib) may be prepared by coupling the compound of formula (IV) with the compounds of formulae (V) and (VI) to form compounds of formulae (IIIa) and (IIIb), respectively and reducing the compounds:

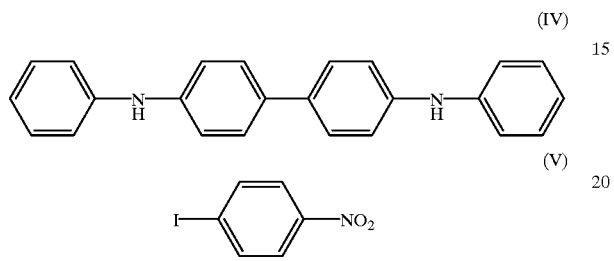
(IV)

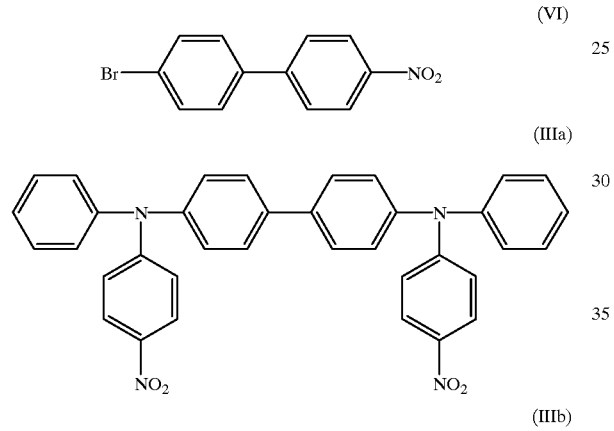
(V)
(VI)
(IIIa)

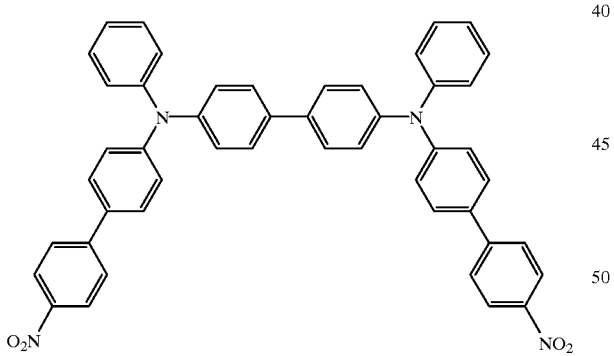
(IIIb)

The bromonitrobiphenyl of formula (VI) may be formed by nitrating bromobiphenyl. The coupling reaction may be conducted in a solvent such as xylene, toluene and dimethylsulfoxide at a temperature ranging from 80 to 180° C., in the presence of a catalyst such as Cu, CuCl and Pd/phosphine.

In addition, the compound of formula (Ib) may be prepared by reacting the secondary amine compound of formula (VII) with a compound of formula (VIII) to form the compound of formulae (IIIb), and reducing the compound:

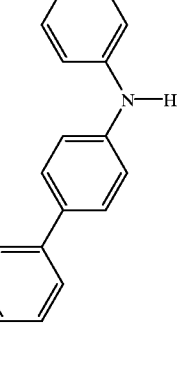
(VII)

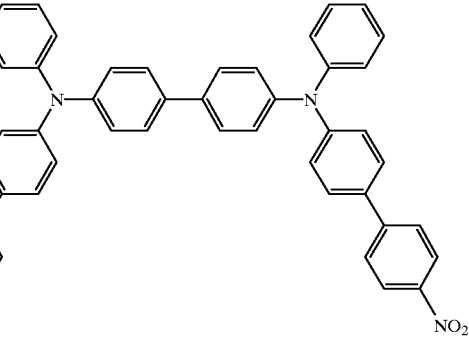
(VIII)
(IIIb)

wherein, X is iodine or bromine.

The secondary amine compound of formula (VII) may be synthesized by reacting aniline with the compound of formula (VI). The reaction between the compounds of formulae (VII) and (VIII) may be carried out in a solvent such as xylene, toluene and dimethylsulfoxide at a temperature ranging from 80 to 180° C., in the presence of a catalyst such as Cu, CuCl and Pd/phosphine.

The inventive diamine derivative of formula (I), e.g., compounds of formulae (Ia), (Ib) and (Ic), prepared in accordance with the above-described method has a high glass transition temperature of 100° C. or higher and exhibits improved hole transporting characteristics. Accordingly, the inventive diamine may fabricate a hole transport layer as is, and, further, be used to form a stable polymer(e.g., polyimide, polyamide and polyurea) hole transport layer.

The organic electroluminescent device of the present invention comprises the inventive diamine derivative of formula (I) as a hole transport agent. The inventive electroluminescent device comprises an organic interlayer which may be of a multi-layer structure containing a hole transport layer and an organic luminescent layer. The organic interlayer may further include an electron transport layer, inserted between the metallic electrode layer and the organic luminescent layer.

An example of the organic electroluminescent device of the present invention contains a triple-layered organic interlayer as shown in FIG. 1. The device consists of a transparent substrate(1), a transparent electrode layer(2), a hole transport layer(3), an organic luminescent layer(4), an electron transport layer(5) and a metallic electrode layer(6). An electric power supply(7) may be either alternating current (AC) or direct current(DC).

The hole transport layer of the present invention may be formed by a conventional method which may be a wet process, e.g., a spin-coating, doctor-blading, roll-printing and screen-printing method, or a dry process, e.g., a vapor deposition, vacuum thermal deposition, sputtering and electron beam deposition method. The thickness of the hole transport layer may range from 5 to 300 nm.

Exemplary electroluminescent materials which may be used in the present invention include tris(8-hydroxyquinolinolato)aluminum ($Alq_3$), 1,1,4,4-tetraphenyl-1,3-butadiene(TB), oligophenylenevinylene derivatives, 4-(dicyanomethylene)-2-methyl-6-(4-dimethylaminostyryl)-4H-pyran(DCM), 1,4-distyrylbenzene, anthracene, tetracene, pentracene, coronene, perylene, pyrene, bis (8-quinolinolato) zinc(II), 9,10-diphenylanthracene, tris (4,4,4-trifluoro-1-(2-thienyl)-1,3-butandiono)-1,10-phenanthroline europium(III), tris(2,4-pentadiono)-1,10-phenanthroline terbium(III), tris(4,4,4-trifluoro-1-(2-thienyl)-1,3-butandiono)-1,10-phenanthroline dysprosium(III), and a mixture thereof. The thickness of the organic luminescent layer may range from 5 to 300 nm.

Exemplary electron transport agents which may be used in the present invention include $Alq_3$, LiF, and oxadiazole derivatives such as 2-(4-biphenyl)-5-(4-tert-butylphenyl)-1,3,4-oxadiazole(B-PBD), 3-(4-biphenylyl)-4-phenyl-5-(4-t-butylphenyl)-1,2,4-triazole(TAZ), 2,5-bis(1-naphtholyl)-1,3,4-oxadiazole(BND), and a mixture thereof. The electron transport layer may be formed on the organic luminescent layer in a thickness ranging from 5 to 300 nm.

The organic electroluminescent device of the present invention has good thermal and mechanical properties, improved stability and prolonged lifetime.

The present invention is further described and illustrated in Example, which is, however, not intended to limit the scope of the present invention.

EXAMPLE 1

Preparation of Compound of Formula (Ia)
(Step 1) Preparation of Compound of Formula (IIIa)

3.364 g of N,N'-diphenylbenzidine (formula (IV)), 5.975 g of iodonitrobenzene (formula (V)), 110 mg of $Pd(OAc)_2$ and 220 mg of tri-o-tolyl phosphine were added to 30 ml of refined toluene, and 2.5 g of sodium-t-butoxide was added thereto under a nitrogen atmosphere. The mixture was heated at 65° C. for 4 hours. Then, the reaction mixture was cooled to room temperature and 100 ml of chloroform was added. The resulting solution was filtered through a silica gel column and the solvent was removed from the filtrate under a reduced pressure to obtain a residue, which was recrystallized from a mixture of acetone and methanol to obtain 4.63 g (yield: 80%) of the title compound (formula (IIIa)) as a yellow solid.

$^1$H-NMR(DMSO-$D_6$): δ 8.09(d,4H), 7.74(d,4H), 7.47(t, 4H), 7.20~7.35(m,10H), 6.87(d,4H).
(Step 2) Preparation of Compound of Formula (Ia)

0.578 g of the compound (formula (IIIa)) obtained in (Step 1) and 0.32 g of 70 % NaSH were added to a mixture of 5 ml of n-butanol and 5 ml of toluene, and the mixture was refluxed for 5 hours. The solvent was removed from the reaction mixture under a reduced pressure and the residue was treated with a mixture of 15 ml of water and 15 ml of chloroform. Subsequently, the mixture was extracted with chloroform (150 ml×3), the organic extracts were combined, and chloroform was removed therefrom under a reduced pressure to obtain 0.43 g (yield: 83%) of the title compound (formula (Ia)).

$^1$H-NMR(DMSO-$D_6$): δ 7.43(d,4H), 7.21(t,4H), 6.58 ~6.95(m,14H), 6.57(d,4H).

Figure 2:
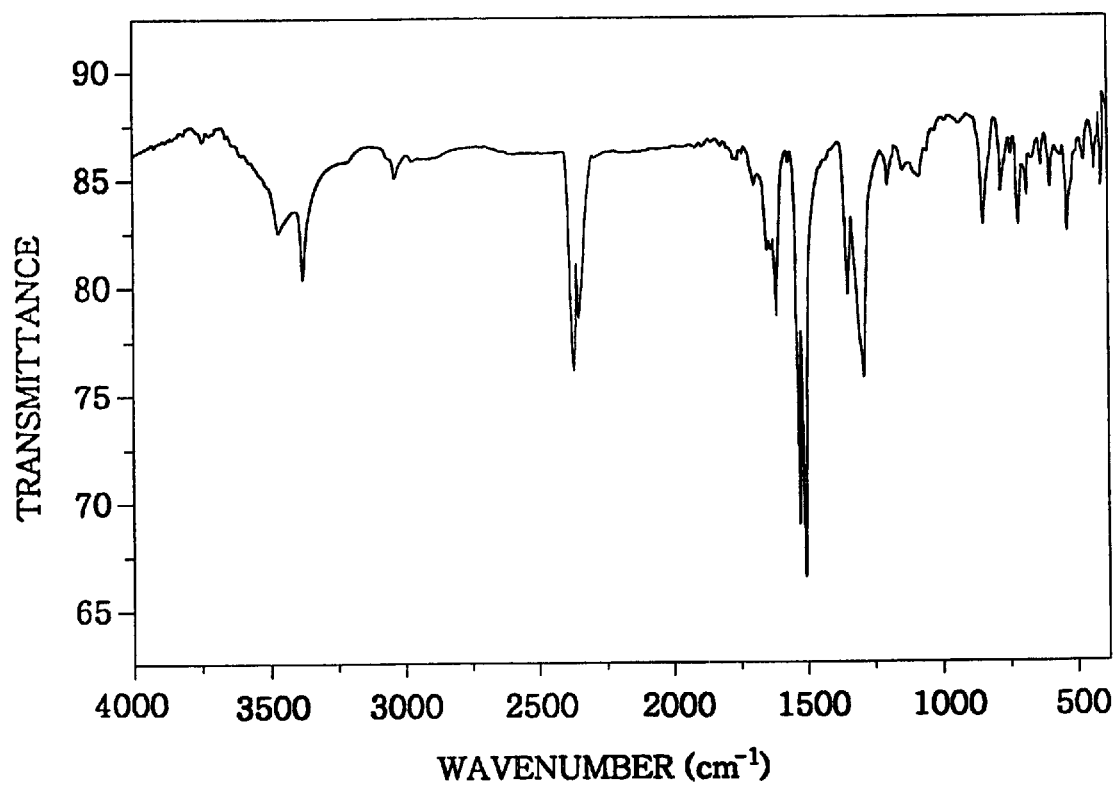
FIG. 2 shows an infrared spectrum of the compound of formula (Ia) prepared in Example 1.

FIG. 2 shows an infrared spectrum of the compound (formula (Ia)) thus obtained.

EXAMPLE 2

Preparation of Compound of Formula (Ib)
(Step 1) Preparation of Compound of Formula (VI)

4.66 g of bromobiphenyl was added to a mixture of 6 g of sulfuric acid and 35 g of acetic acid, and 2.2 g of 60% $HNO_3$ was added slowly thereto at 25° C. for 5 min. The mixture was heated at 750 ° C. for 4 hours. Then, the reaction mixture was cooled to room temperature and the precipitates were filtered, washed with water and dried to obtain 4.40 g (yield: 80%) of the title compound (formula (VI)) as a white solid.

$^1$ H-NMR($CDC_13$): δ 8.31 (d,4H), 7.71(d,4H), 7.63(d, 4H), 7.49(d,4H).
(Step 2) Preparation of Compound of Formula (IIIb)

2.92 g of the compound (formula (VI)) obtained in (Step 1), 1.68 g of N,N'-diphenylbenzidine (formula (IV)), 55 mg of $Pd(OAc)_2$ and 220 mg of tri-o-tolyl phosphine were added to 10 ml of refined xylene, and 1.25 g of sodium-t-butoxide was added thereto under a nitrogen atmosphere. The mixture was heated at 120° C. for 3 hours. Then, the reaction mixture was cooled to room temperature and 50 ml of chloroform was added thereto. The resulting solution was filtered and the solvent was removed from the filtrate under a reduced pressure and the residue was purified by column chromatography (eluent; chloroform:n-hexane=1.1) to obtain 2.63 g (yield: 72%) of the title compound (formula (IIIb)).

$^1$H-NMR(DMSO-$D_6$):δ 8.26 (d,4H), 7.92(d,4H), 7.74(d, 4H), 7.63(d,4H), 7.38(t,4H), 7.07~7.15(m,14H).
(Step 3) Preparation of Compound of Formula (Ib)

1.46 g of the compound (formula (IIIb)) obtained in (Step 2) and 0.64 g of 70% NaSH were added to a mixture of 25 ml of n-butylalcohol and 2 ml of water, and the mixture was heated at 110° C. for 24 hours. The solvent was distilled off under a reduced pressure. The resulting residue was treated with 10 ml of water, filtered, and dried to obtain 1.16 g (yield: 91%) of the title compound (formula (Ib)).

$^1$H-NMR(DMSO-$D_6$) δ7.55(d,4H), 7.48(d,4H), 7.28 ~7.31(m,8H), 7.02 ~7.07(m,14H), 6.61(d,4H).

Figure 3:
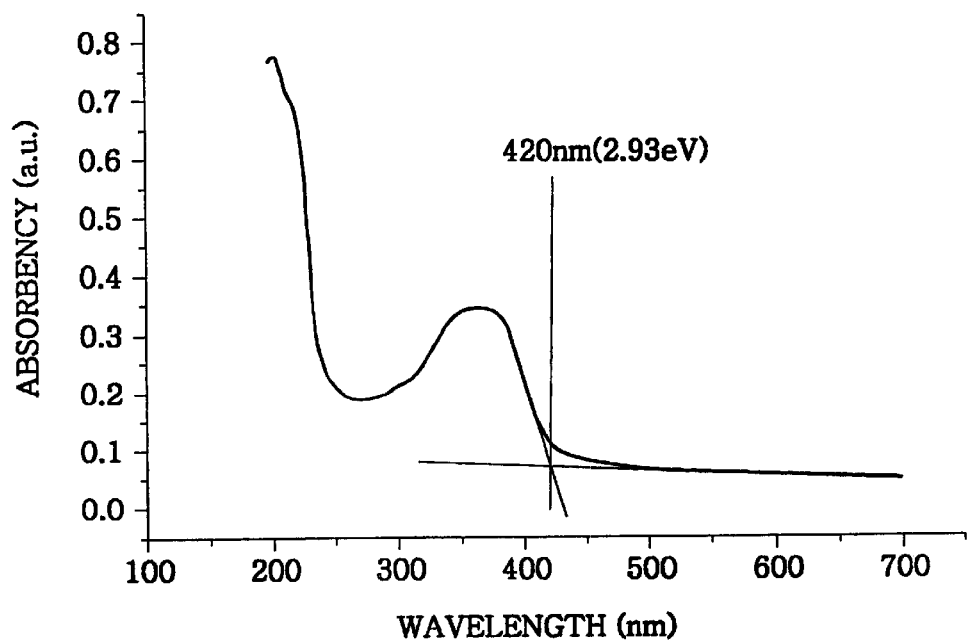
FIG. 3 reproduces an absorption spectrum of the compound of formula (Ib) prepared in Example 2.
Figure 4:
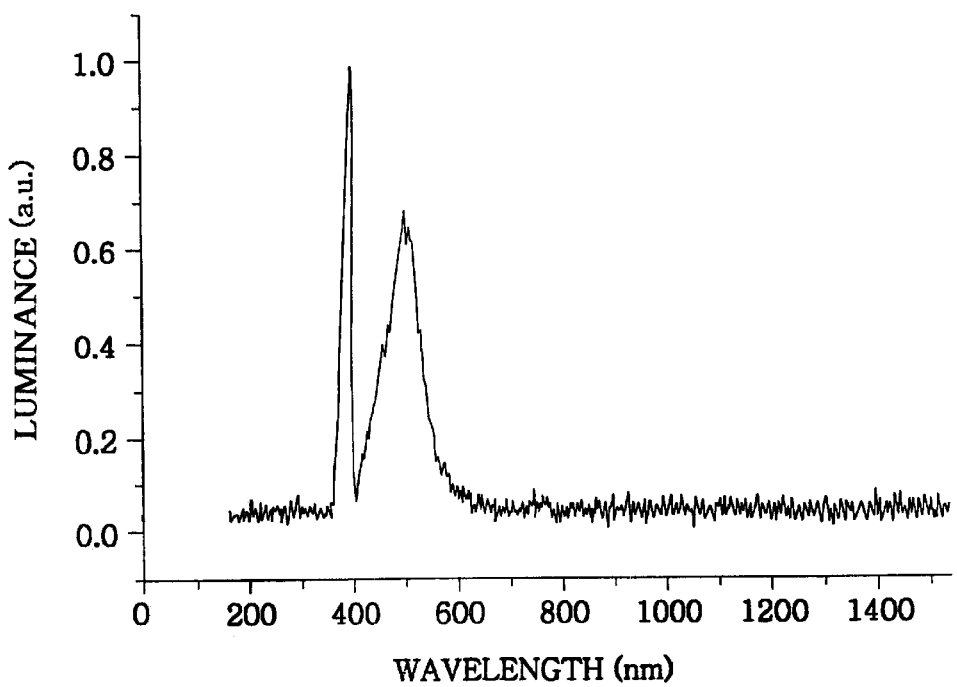
FIG. 4, a luminescent spectrum of a thin layer made thereof.

An absorption spectrum of the compound (formula (Ib)) thus obtained is shown in FIG. 3; and a luminescent spectrum of a thin layer thereof prepared by vapor deposition, in FIG. 4.

EXAMPLE 3

Preparation of Compound of Formula (Ic)
(Step 1) Preparation of Compound of Formula (IIc)

7.023 g of carbazole, 8.12 g of 4,4'-diodobiphenyl, 5.528 g of $K_2CO_3$ and 0.396 g of CuCl were added to 20 ml of DMSO, under a nitrogen atmosphere. The mixture was heated at 140° C. for 1 hour, and then at 170° C. for 3 hours. Then, the reaction mixture was cooled to below 50° C. and 100 ml of water was added thereto. The resulting solution was stirred for 30 min. and filtered. The filtrate was dried to produce a solid, which was dissolved in 100 ml of methanol. The solution was refluxed for 30 min. and filtered. The resulting filtrate was dried to obtain 9.49 g (yield: 98%) of the title compound (formula (IIc)) as a light gray solid.

$^1$H-NMR(CDC$l_3$):δ 8.18 (d, 4H), 7.92(d,4H), 7.72(d, 4H), 7.52(d,4H), 7.45(t,4H), 7.32(t,4H)

(Step 2) Preparation of Compound of Formula (IIIC)

4.855 g of the compound (formula (IIc)) obtained in (Step 1) and 2.31 g of 60% HNO$_3$ were added to 100 ml of acetic acid. The mixture was heated at 65 ° C. for 2 hours. Then, the reaction mixture was cooled to room temperature, and the solid formed was filtered, washed with water and dried to obtain 5.46 g (yield: 95%) of the title compound (formula (IIIc)) as a light yellow.

$^1$H-NMR(CDCl$_3$): δ 9.12(s,2H), 8.38(d,2H), 8.26(d,2H), 7.97(d,4H), 7.73(d,4H), 7.48~7.53(m,8H)

(Step 3) Preparation of Compound of Formula (Ic)

0.575 g of the compound (formula (IIIc)) obtained in (Step 2) and 0.64 g of 70% NaSH were added to 20 ml of n-butanol, and the mixture was refluxed for 3 hours. The solvent was removed from the reaction mixture under a reduced pressure. The solid thus obtained was treated with 20 ml of water, filtered, dried and purified by column chromatography (eluent; chloroform:n-hexane=1:1) to obtain 0.42 g (yield: 82%) of the title compound (formula (Ic)).

$^1$H-NMR(DMSO-D$_6$): δ 8.04(d,4H), 7.73(d,4H), 7.16~7.47(m,12H), 6.81(d,2H).

Figure 5:
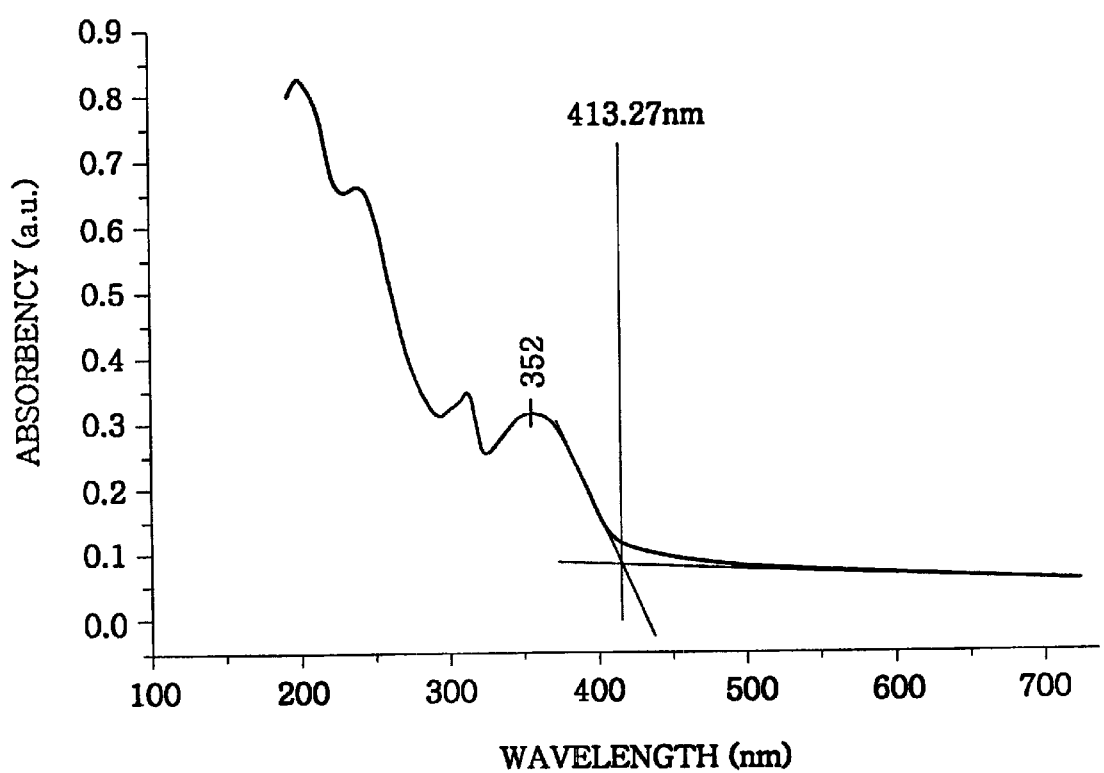
FIGS. 5 and 6 exhibit absorption and infrared spectra of the compound of formula (Ic) prepared in Example 3, respectively.
Figure 6:
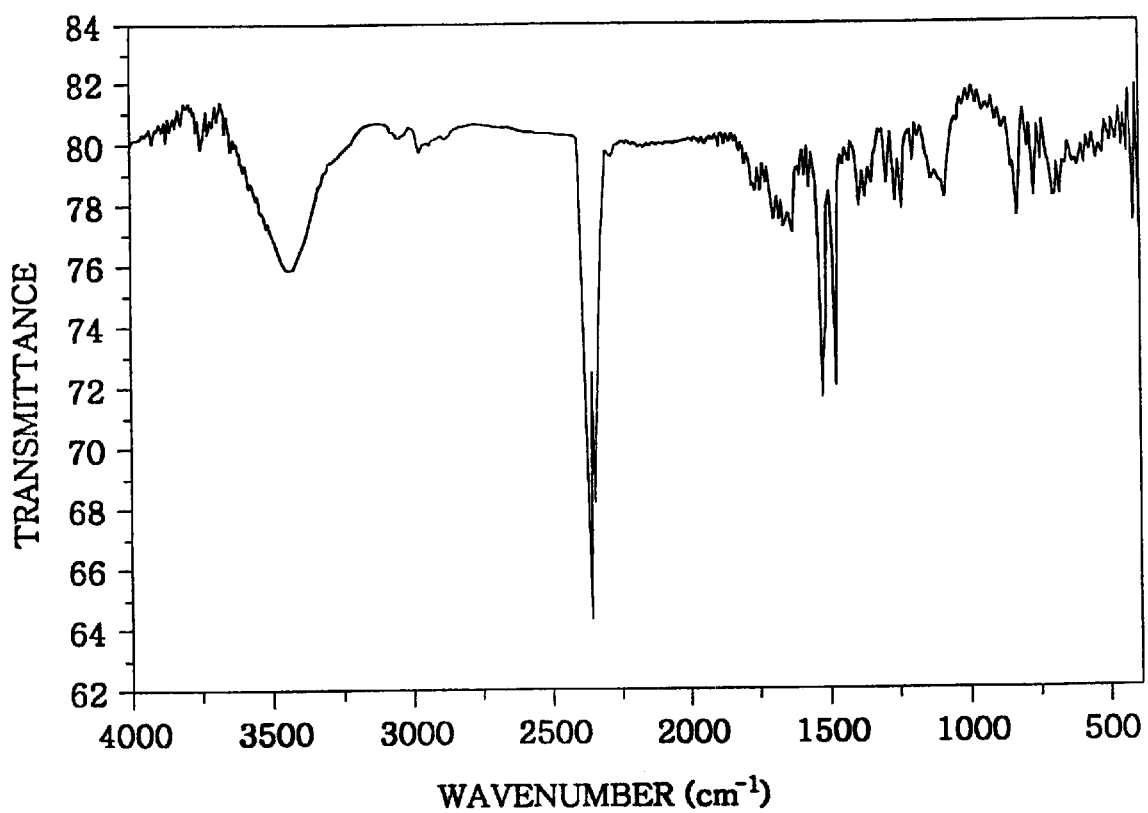
Figure 7:
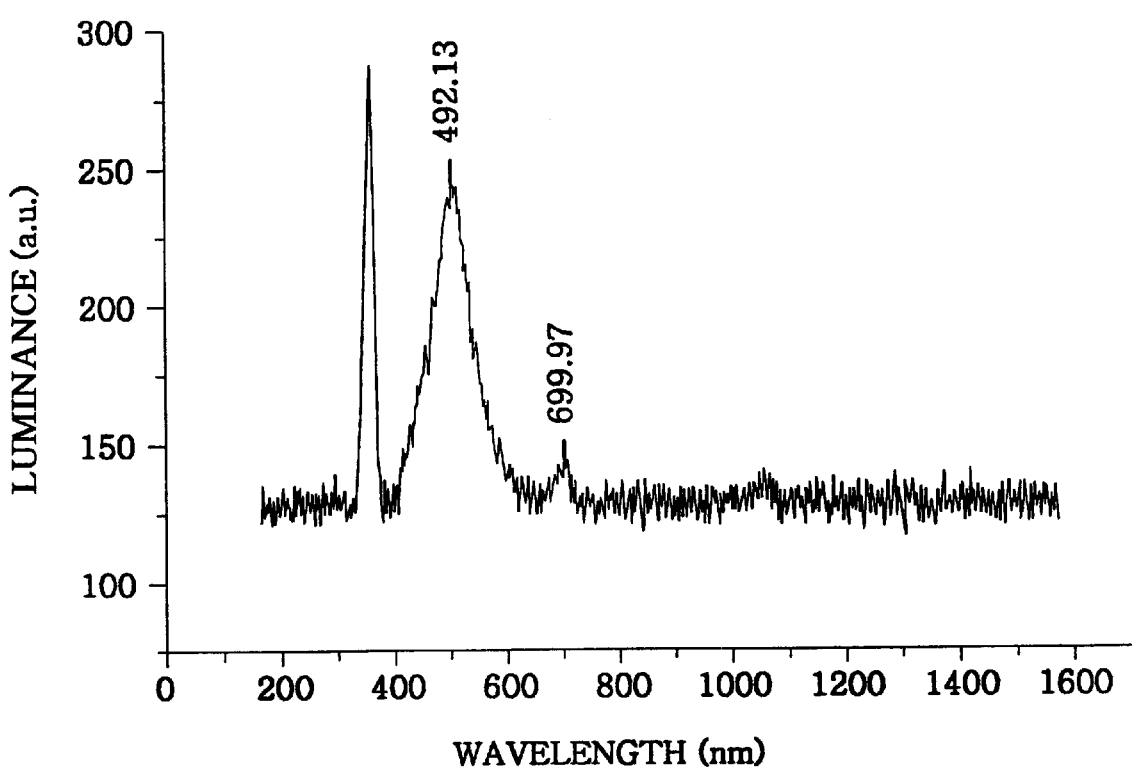
FIG. 7, a luminescent spectrum of a thin layer made thereof.

Absorption and infrared spectra of the compound (formula (Ic)) thus obtained are shown in FIGS. 5 and 6, respectively; and a luminescent spectrum of a thin layer thereof prepared by vapor deposition, in FIG. 7.

EXAMPLE 4

Preparation of an Organic Electroluminescent Device—(1)

Indium-tin-oxide(ITO) was coated on a glass substrate to form a transparent anode layer. The compound of formula (Ib) obtained in Example 2 was vapor deposited on the transparent anode layer to a thickness of 30 nm at a rate of 0.03 nm/sec at 5×10$^{-6}$ torr to form a hole transport layer. Then, Alq$_3$ was vapor deposited on the hole transport layer to a thickness of 20 nm at a rate of 0.03 nm/sec at 5×10$^{-6}$ torr to form a luminescent/electron transport layer. Subsequently, aluminum was vapor deposited on the luminescent/electron transport layer to a thickness of 300 nm at a rate of 1 nm/sec at 2×10$^{-5}$ torr to form a cathode layer.

Figure 8:
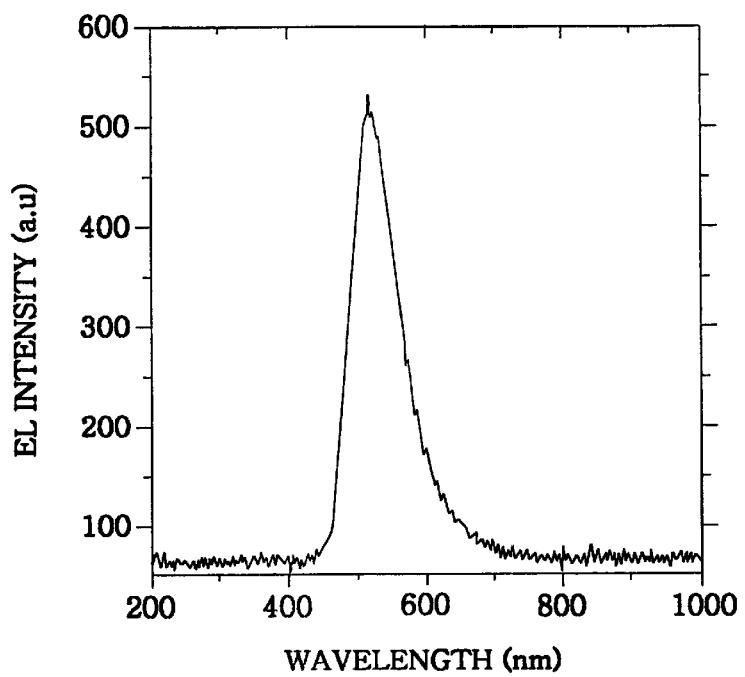
FIG. 8 shows an electroluminous spectrum of the electroluminescent device prepared in Example 4.
Figure 9:
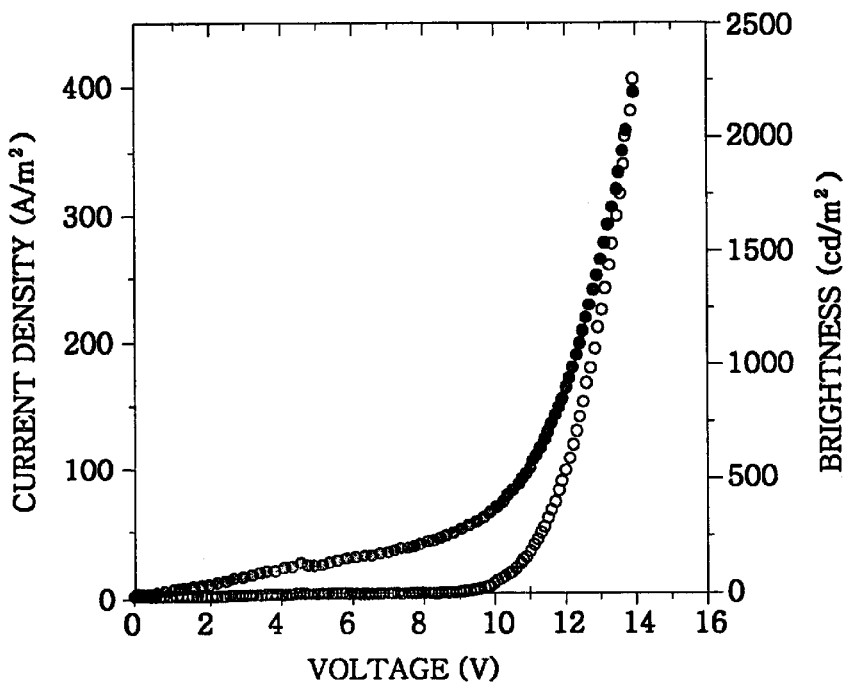
FIG. 9, variations of the current density($A/m^2$) (●) and brightness($cd/m^2$) (○) as function of the applied voltage(V)
Figure 10:
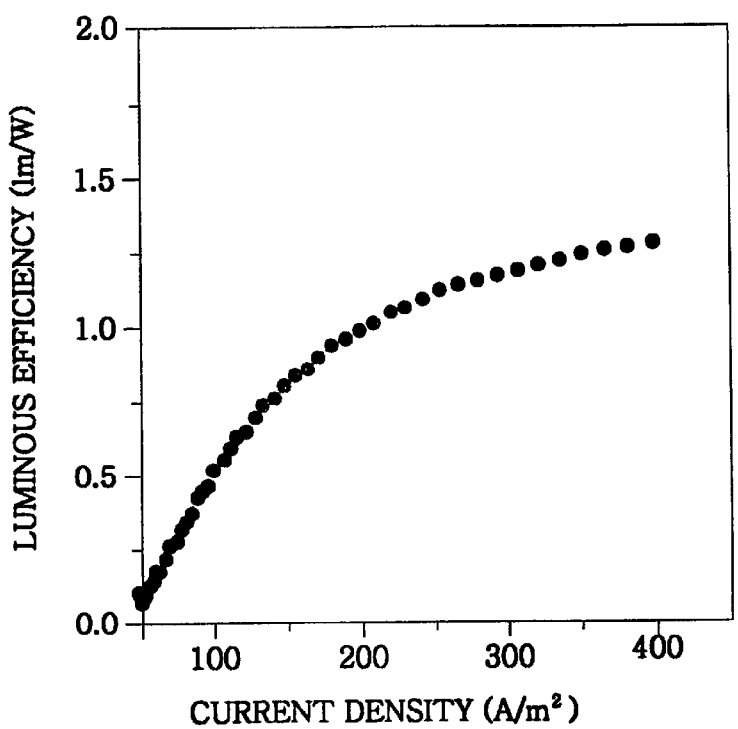
FIG. 10, the change in the luminous efficiency(lm/W) with current density($A/m^2$)

The luminescence characteristics of the organic electroluminescent device thus obtained are shown in FIGS. 8, 9 and 10.

FIG. 8 reproduces an electroluminous spectrum of the electroluminescent device.

FIG. 9 illustrates the variations of the current density(A/m$^2$) (●) and brightness(cd/m$^2$) (○) of the electroluminescent device as function of the applied voltage (V). The current injection starts at about 2V, turn on voltage is about 8 to 9V, and the brightness is 500 cd/m$^2$ at 12V.

FIG. 10 exhibits the change in the luminous efficiency (lm/W) of the electroluminescent device with current density(A/m$^2$). The luminous efficiency is steady at 1.2 lm/W at a current density of 300 A/m$^2$ and beyond.

EXAMPLE 5

Preparation of an Organic Electroluminescent Device—(2)

Indium-tin-oxide(ITO) was coated on a glass substrate to form a transparent anode layer. The compound of formula (Ic) obtained in Example 3 was vapor deposited on the transparent anode layer to a thickness of 50 nm at a rate of 0.03 nm/sec at 5×10$^{-6}$ torr to form a hole transport layer. Then, Alq$_3$ was vapor deposited on the hole transport layer to a thickness of 20 nm at a rate of 0.03 nm/sec at 5×10$^{-6}$ torr to form a luminescent/electron transport layer. Subsequently, aluminum was vapor deposited on the luminescent/electron transport layer to a thickness of 300 nm at a rate of 1 nm/sec at 2×10$^{-5}$ torr to form a cathode layer.

Figure 11:
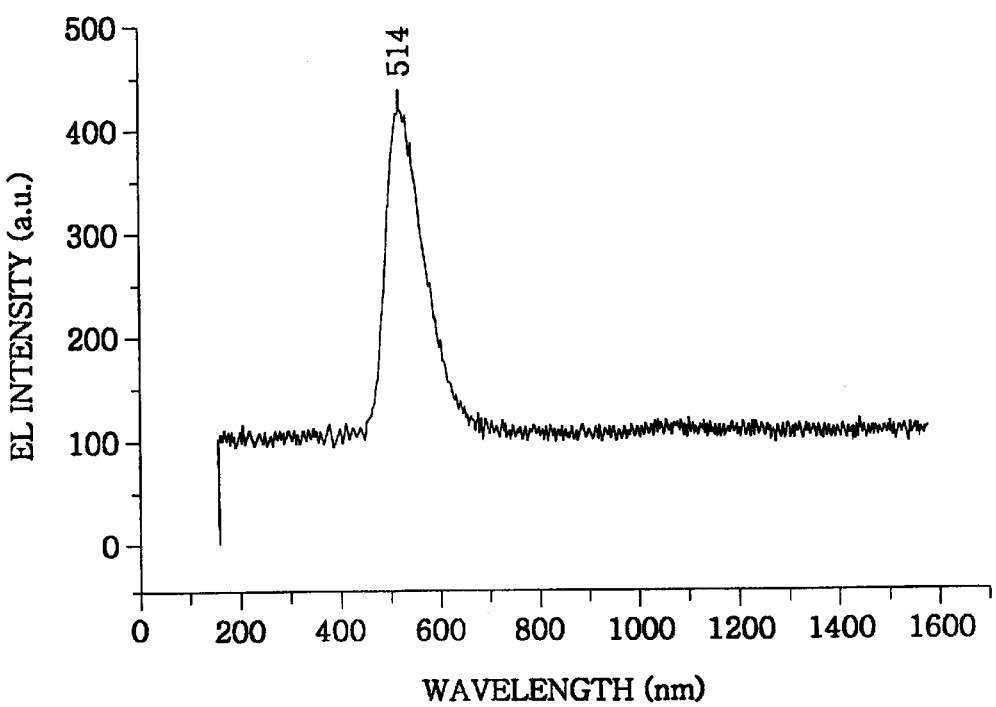
FIGS. 11 and 12 depict an electroluminescent spectrum of the electroluminescent device prepared in Example 5, and variations of the current density($A/m^2$) (12-1) and brightness ($cd/m^2$) (12-2) with the applied voltage(V), respectively.
Figure 12:
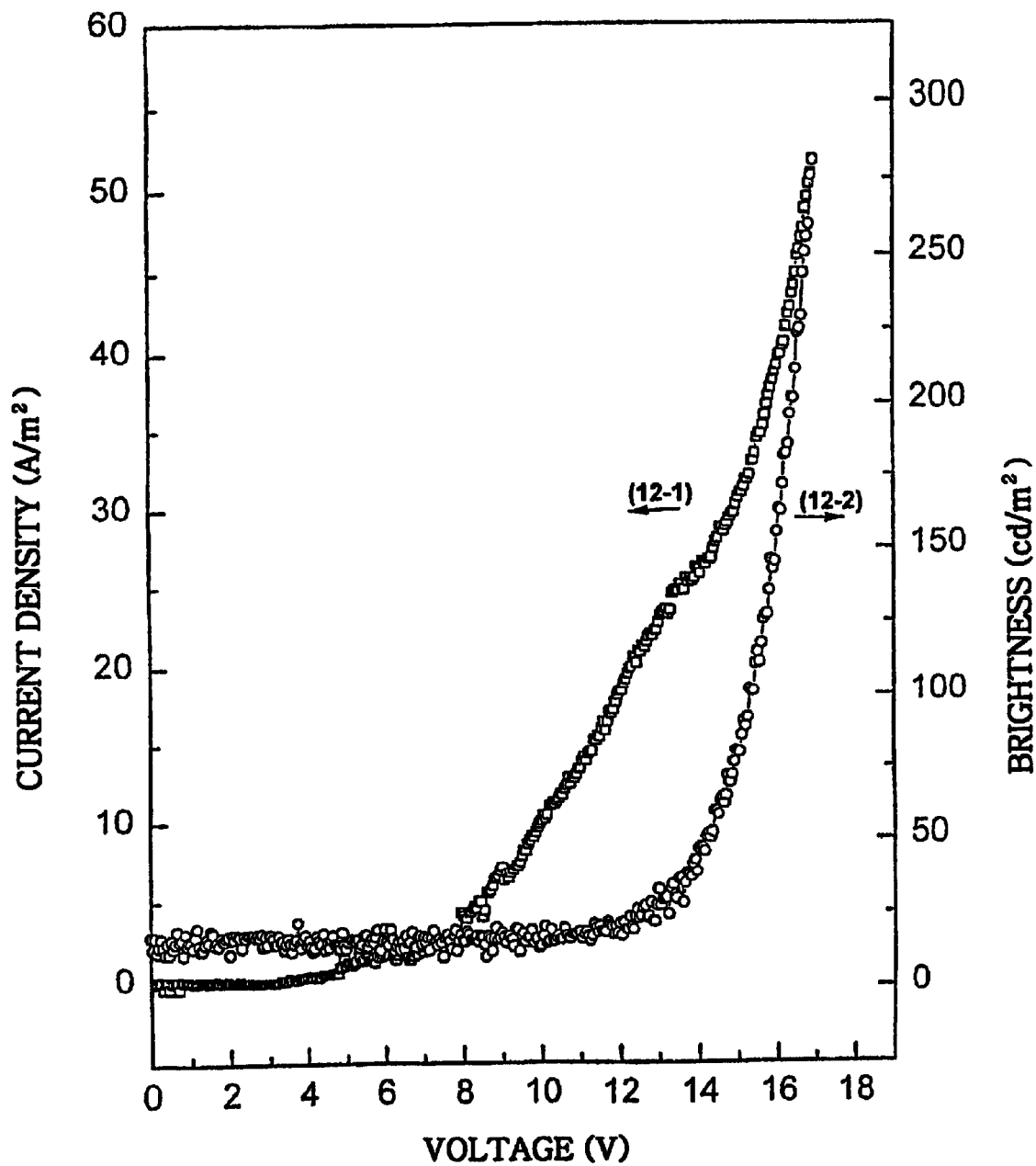

The luminescence characteristics of the organic electroluminescent device thus obtained are shown in FIGS. 11 and 12.

FIG. 11 depicts an electroluminescent spectrum of the electroluminescent device.

FIG. 12 shows the variations of the current density(A/m$^2$) (12-1) and brightness(cd/m$^2$) (12-2) of the above electroluminescent device as function of the applied voltage (V). The current injection starts at about 6V, turn on voltage is about 7 to 8V, and the brightness is 200 cd/m2 at 16V.

As can be seen from the above result, an organic electroluminescent device containing the novel hole transport agent of the present invention has an improved luminous efficiency. Also, the inventive electroluminescent device has an improved stability and prolonged lifetime due to the high glass transition temperature of the inventive hole transport agent. Therefore, the inventive electroluminescent device may be advantageously applied to solar cells, photorefraction thin layer devices, organic photoconductors, field effect transistors, photodiodes and the like.

While the invention has been described with respect to the specific embodiments, it should be recognized that various modifications and changes may be made by those skilled in the art to the invention which also fall within the scope of the invention as defined by the appended claims.

What is claimed is:

1. The diamine compound of formula (Ic):

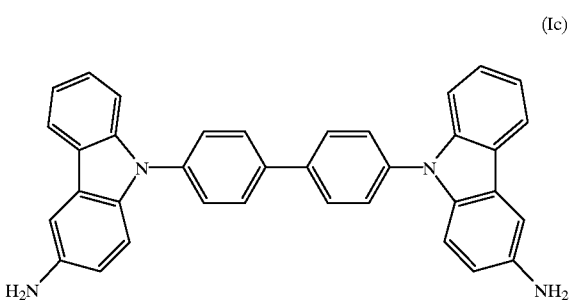

(Ic)

2. An organic electroluminescent device comprising a hole transport layer containing the diamine compound of claim 1.

* * * * *

UNITED STATES PATENT AND TRADEMARK OFFICE
CERTIFICATE OF CORRECTION

PATENT NO. : 6,337,404 B1
DATED : January 8, 2002
INVENTOR(S) : Ki-Jong Han et al.

It is certified that error appears in the above-identified patent and that said Letters Patent is hereby corrected as shown below:

<u>Title page,</u>
Inventors, change "Ki-jong Han" to -- Ki-Jong Han --.

Signed and Sealed this

Fourth Day of June, 2002

Attest:

Attesting Officer

JAMES E. ROGAN
*Director of the United States Patent and Trademark Office*